(12) United States Patent
Suzuki (10) Patent No.: US 7,204,846 B2
(45) Date of Patent: Apr. 17, 2007

(54) BEAUTY DEVICE (75) Inventor: Shuhei Suzuki, Tokyo (JP)

(73) Assignee: Futek, Inc., Tokyo (JP)

( * ) Notice: Subject to any disclaimer, the term of this patent is extended or adjusted under 35 U.S.C. 154(b) by 252 days.

(21) Appl. No.: 10/893,245

(22) Filed: Jul. 19, 2004

(65) Prior Publication Data
US 2005/0131497 A1    Jun. 16, 2005

(30) Foreign Application Priority Data
Dec. 12, 2003 (JP) .............................. 2003-414886

(51) Int. Cl.
*A61N 5/06* (2006.01)
*A61B 18/18* (2006.01)

(52) U.S. Cl. ..................... 607/88; 607/90; 607/10; 606/9; 606/32; 606/41

(58) Field of Classification Search ............ 607/88–91; 606/8–12, 32–50
See application file for complete search history.

(56) References Cited
U.S. PATENT DOCUMENTS 6,022,455 A * 2/2000 Otake ....................... 204/157.6
6,053,909 A * 4/2000 Shadduck ...................... 606/3
6,443,978 B1 * 9/2002 Zharov ........................ 607/91
6,860,896 B2 * 3/2005 Leber et al. .................... 607/1
6,939,344 B2 * 9/2005 Kreindel ........................ 606/9
2005/0085806 A1 * 4/2005 Auge et al. ................... 606/32
2005/0107853 A1 * 5/2005 Krespi et al. ................. 607/89

* cited by examiner

*Primary Examiner*—A. Farah
(74) *Attorney, Agent, or Firm*—Wenderoth, Lind & Ponack, L.L.P.

(57) ABSTRACT

A beauty device includes a light irradiation section that irradiates light of a predetermined wavelength, and an ion generating section that generates an ion. The light irradiation section is placed at one side surface of a main body of the beauty device, and the ion generating section is placed at the other side surface of the main body of the beauty device. The light irradiation section includes a plurality of light source modules arranged in a predetermined array. Each light source module includes a plurality of light emitting diodes that are arranged in a predetermined array to emit light of two or more wavelengths.

6 Claims, 8 Drawing Sheets

20a···644nm (RED)
20b···575nm (YELLOW)
20c···940nm (INFRARED)
20d···870nm (INFRARED)

FIG. 5

AC MODE, E=30ms, F=50ms, FREQUENCY 12.5Hz

BEAUTY DEVICE

BACKGROUND OF THE INVENTION

1. Field of the Invention

The present invention relates to a beauty device that can obtain a beautiful skin effect by applying light of a predetermined wavelength and an ion to reduce blemishes and wrinkles.

2. Description of the Related Art

Various types of beauty devices that provide an effect on a beautiful skin and the like have been conventionally known. For example, Unexamined Japanese Patent Publication 2000-217938 (document 1) discloses that a beautiful skin effect is obtained by irradiating human skin with a laser beam.

Moreover, Unexamined Japanese Utility Model Publication 7-12138 (document 2) discloses that LEDs are blinked to irradiate human eyes with light, thereby improving intraocular blood flow circulation to ease eyestrain.

However, the conventional beauty device was limited to one that provided a laser beam irradiation and used only one predetermined wavelength or carried ultraviolet rays. For this reason, the beautiful skin effect was insufficient and a fixed skill (with expert knowledge) was required in some cases.

SUMMARY OF THE INVENTION

The present invention has been made with consideration given to the aforementioned circumstances. Accordingly, an object of the present invention is to provide a beauty device that can be used safely at home or by individuals and the like to provide a sufficient beautiful skin effect.

A first aspect of the present invention provides a beauty device which includes a light irradiation section that irradiates light of a predetermined wavelength. The beauty device further includes an ion generating section that generates an ion. The light irradiation section is placed at one side surface of a main body of the beauty device, and the ion generating section is placed at the other side surface of the main body of the beauty device. The light irradiation section includes a plurality of light source modules arranged in a predetermined array. Each light source module includes a plurality of light emitting diodes that are arranged in a predetermined array to emit light of two or more wavelengths.

A second aspect of the present invention adopts a configuration, in accordance with the first aspect, wherein the ion generating section includes one electrode to which a cloth impregnated with a vitamin solution is attached and another electrode provided at a holding section of the main body, a power source, and an ion control section. Further, the ion control section applies a pulse wave of a predetermined voltage between one and the other electrodes.

A third aspect of the present invention adopts a configuration, in accordance with the second aspect, wherein the ion control section applies the pulse wave of voltage of 3 to 10 V with a frequency of 0.5 to 2 KHz, a distance of 500 to 700 µs and a width of 300 to 500 µs per pulse.

A fourth aspect of the present invention adopts a configuration, in accordance with the third aspect, wherein the ion control section provides a plurality of pulse widths and pulse distances.

A fifth aspect of the present invention adopts a configuration, in accordance with the first aspect, wherein the light emitting diodes emit yellow light, red light and infrared light at a predetermined pulse.

A sixth aspect of the present invention adopts a configuration, in accordance with the fifth aspect, wherein the light emitting diode emit light of the respective colors with a time difference for each color.

According to the invention of the first aspect, although either one of the ion generating section placed at one side of the main body of the beauty device and the light irradiation section placed at the other side of the beauty device is put onto a skin of the human body, the light irradiation of a predetermined wavelength and the supply of ion can be executed by one equipment.

When the light irradiation section is put onto the skin, a fibroblast of the skin is stimulated by light of two or more wavelengths to make it possible to sufficiently reduce wrinkles and blemishes. Moreover, since the light source modules do not emit ultraviolet rays, a fixed skill (with expert knowledge) is not required at the time of using the device, making it possible to safely use the device at home.

The ion generating section supplies an ion onto the skin, a cosmetic lotion, a cosmetic cream and the like are put on the skin smoothly, and a facial cleansing effect that reveals fine dirt and dust adhered on the skin is brought about, thereby making it possible to obtain a lustrous skin, which is so-called a feeling of smooth.

According to the invention of the second aspect, the same effect as that of first aspect can be obtained, and the ion generating section can ionize the vitamin solution onto the skin to improve absorptivity of the vitamin solution to the skin.

According to the invention of the third aspect, the same effect as that of the second aspect can be obtained, the voltage of each range, the frequency and the pulse are set, making it possible to cause the ion to act on the skin effectively and safely.

According to the invention of the fourth aspect, the same effect as that of the third aspect can be obtained, and the user can select the preset pulse width and distance of the ion control section, so that the ion supply can be easily adjusted according to the individual skin condition.

According to the invention of the fifth aspect, the same effect as that of the first aspect can be obtained, and when the device is put onto the skin, the stimulate the nerve block is stimulated by the yellow light, red light and near infrared light, making it possible to reduce blemishes and wrinkles effectively.

According to the invention of the sixth aspect, the same effect as that of the fifth aspect can be obtained, and light of the respective wavelengths is emitted onto the skin sequentially to obtain a beautiful skin, making it possible to provide effective stimulation.

BRIEF DESCRIPTION OF THE DRAWINGS

These and other objects and advantages of the present invention will become more apparent upon reading of the following detailed description and the accompanying drawings, in which:

FIG. 3 is a view relating to the beauty device according to the embodiment of the present invention, where (a) is a side view, (b) is a front view, where (c) is a rear view;

FIG. 4 is a view illustrating a light source module, and (a) is a plan view seen in a state that a translucent plate is detached, and (b) and (c) are views each illustrating an array of LEDs;

DETAILED DESCRIPTION OF THE PREFERRED EMBODIMENT

An embodiment of the present invention will be explained with reference to the accompanying drawings.

Figure 1:
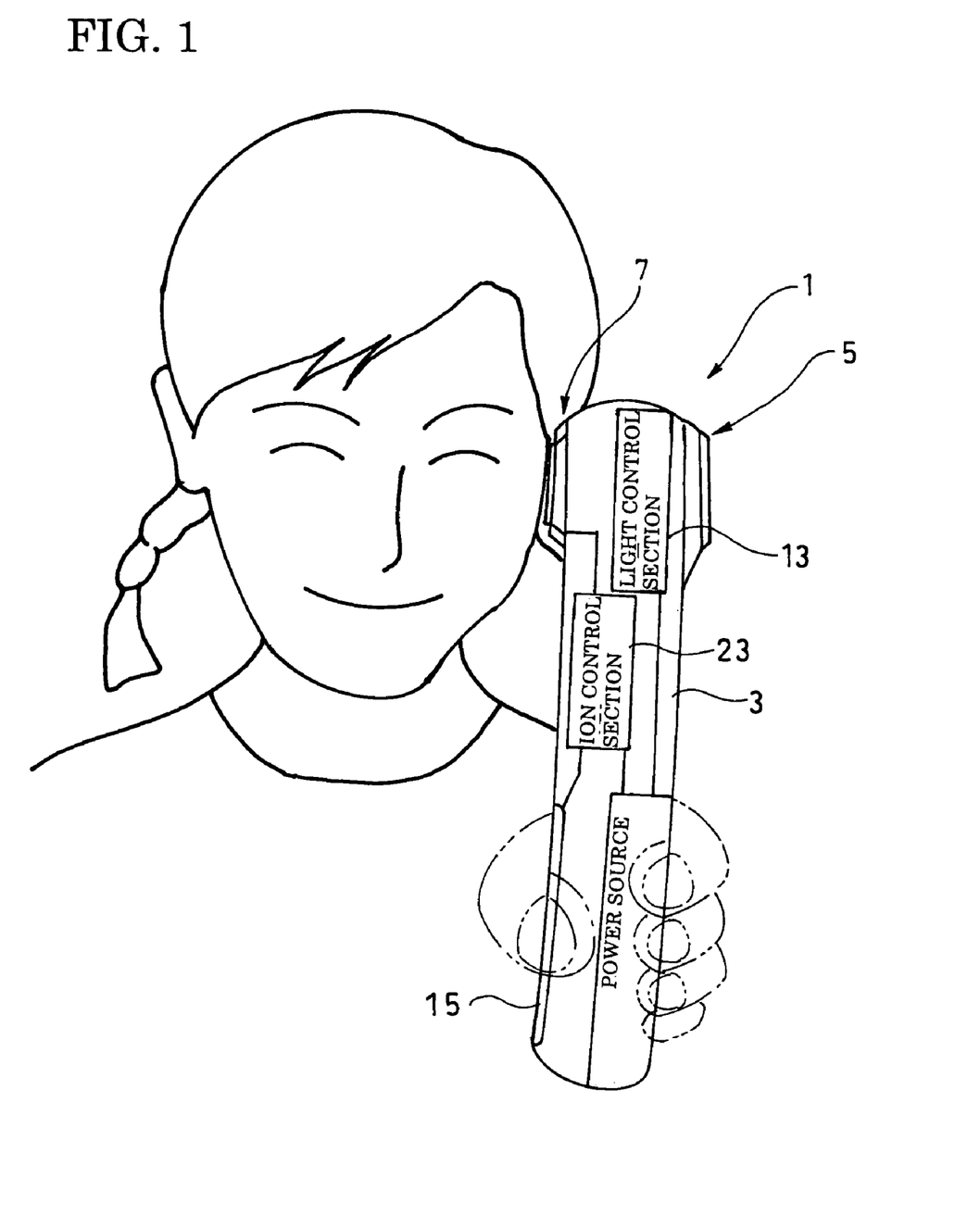
FIG. 1 is a schematic view illustrating a using state and a configuration of a beauty device according to an embodiment of the present invention.
Figure 2:
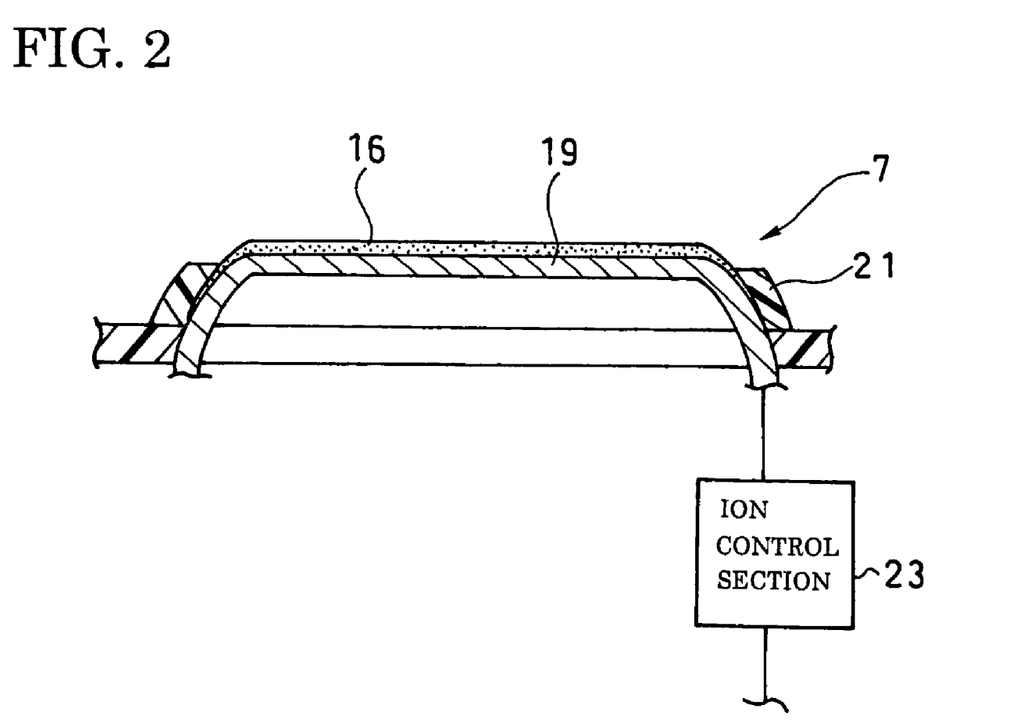
FIG. 2 is a cross-sectional view illustrating a configuration of an ion generating section.
Figure 3A:
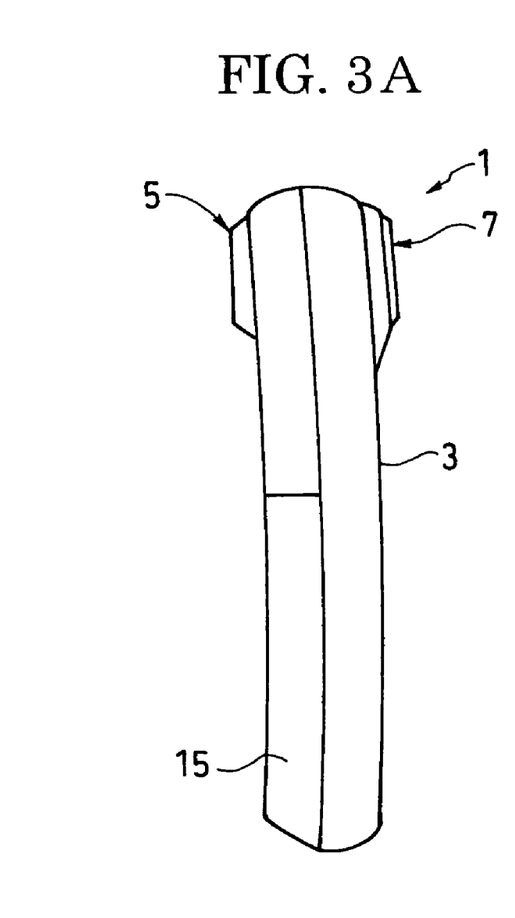
Figure 3B:
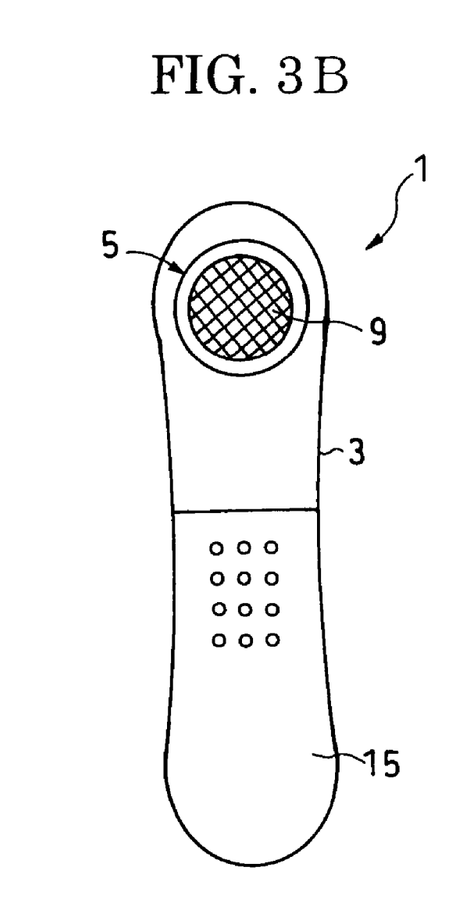
Figure 3C:
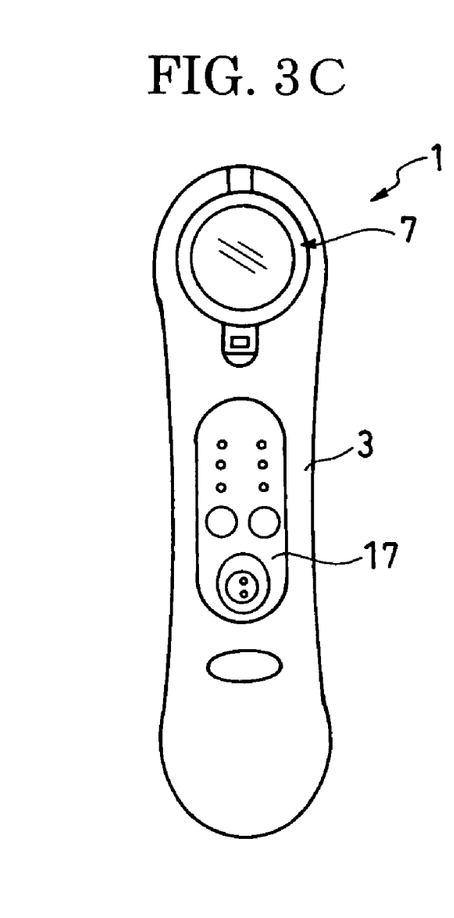
Figure 4A:
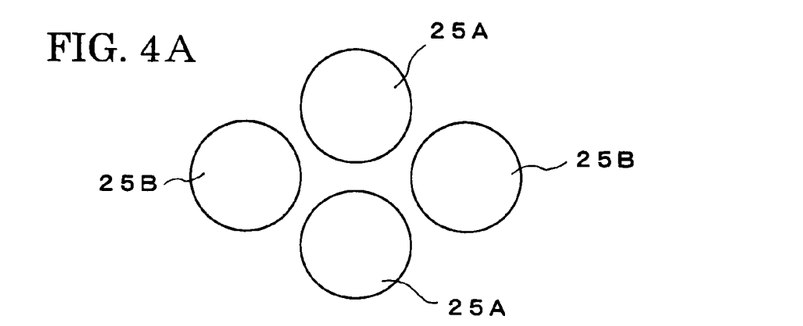
Figure 4B:
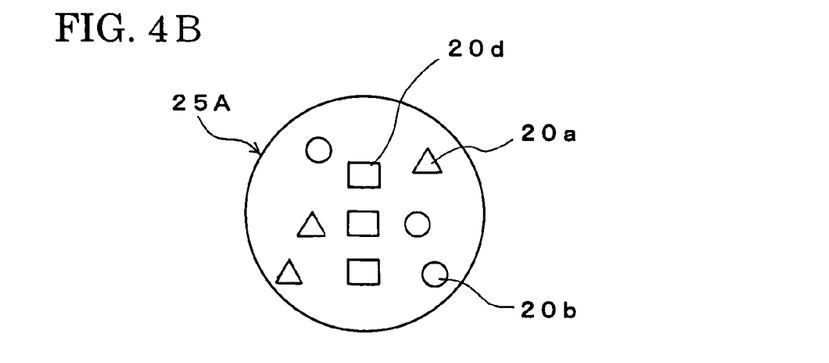
Figure 4C:
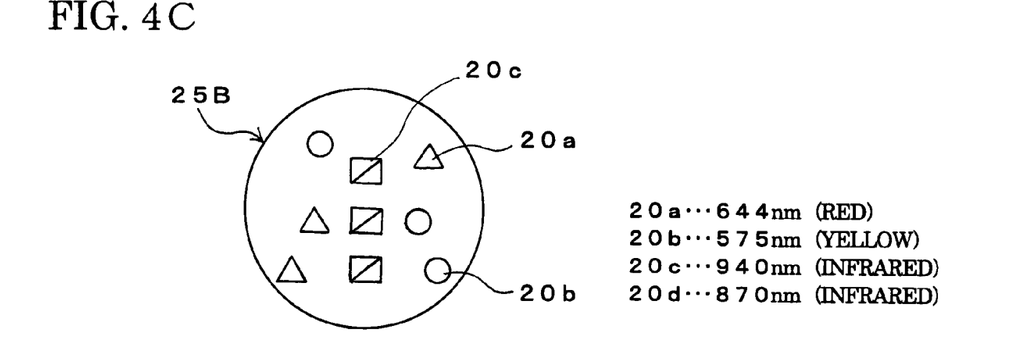
Figure 5:
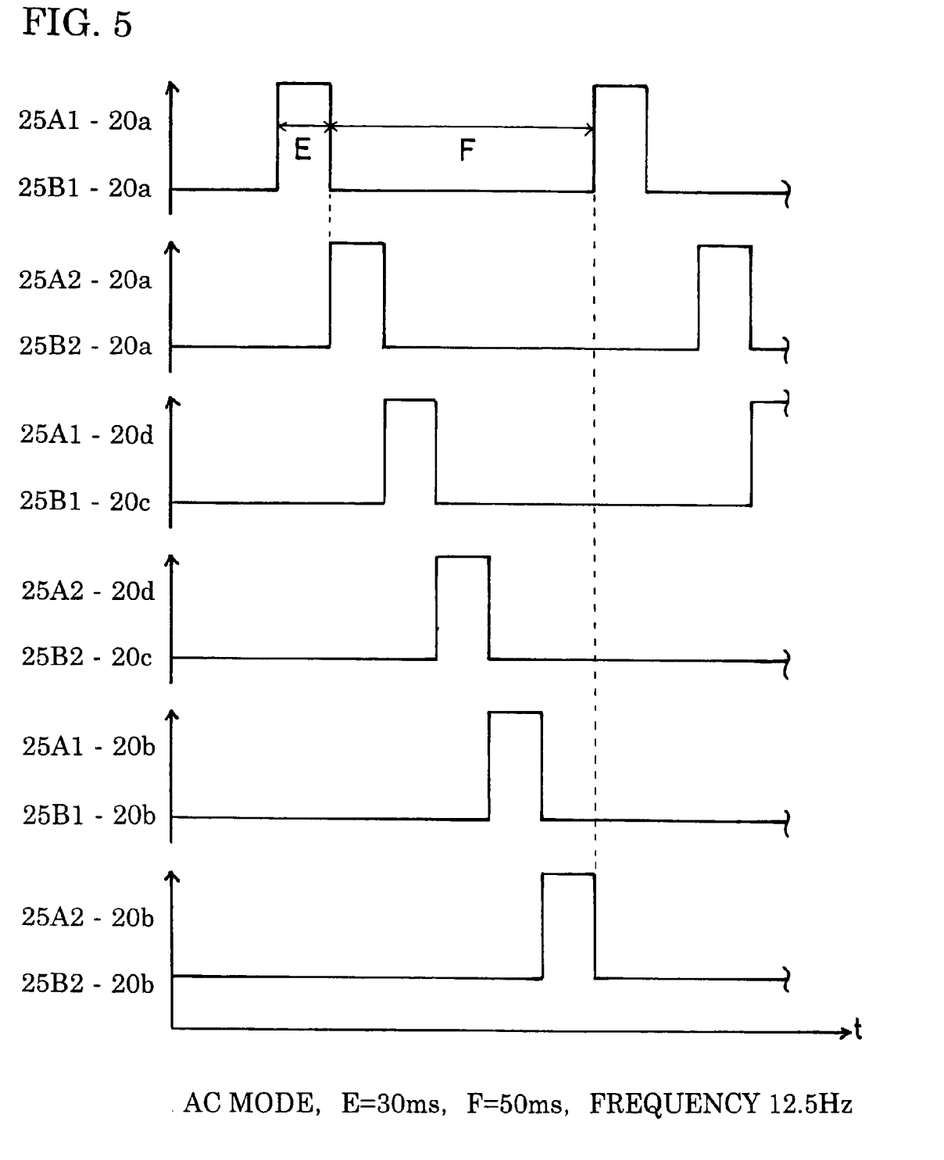
FIG. 5 is a view of a pulse signal that controls blinking of LEDs.
Figure 6:
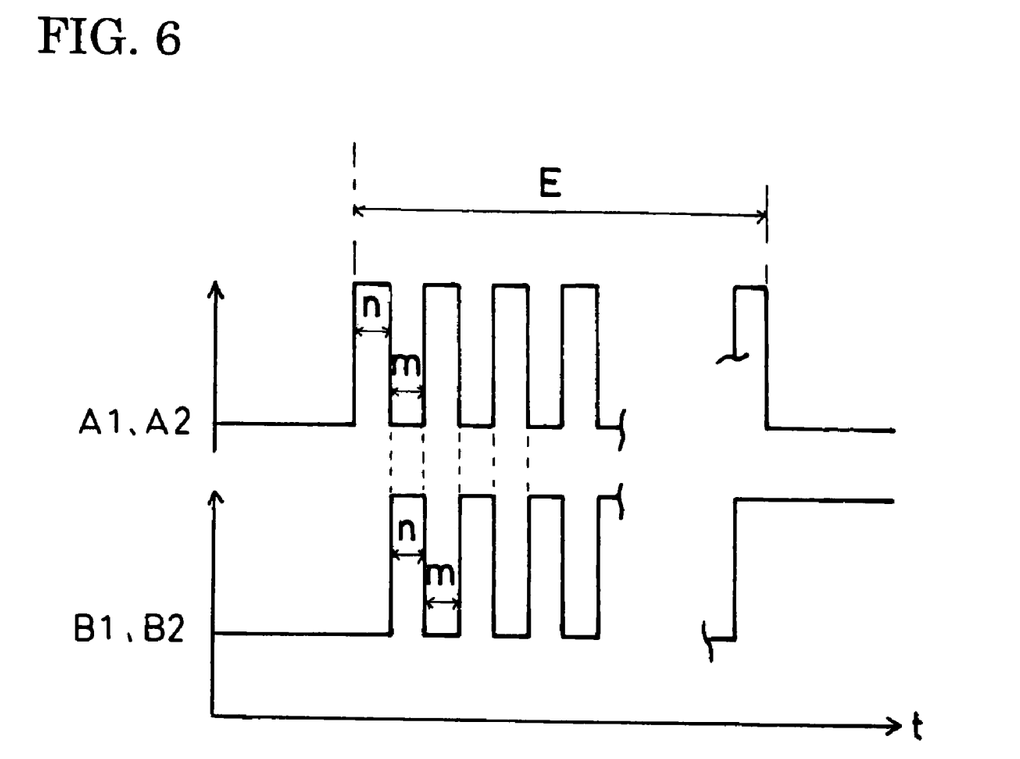
FIG. 6 is a view of a pulse signal that controls blinking of LEDs.
Figure 7:
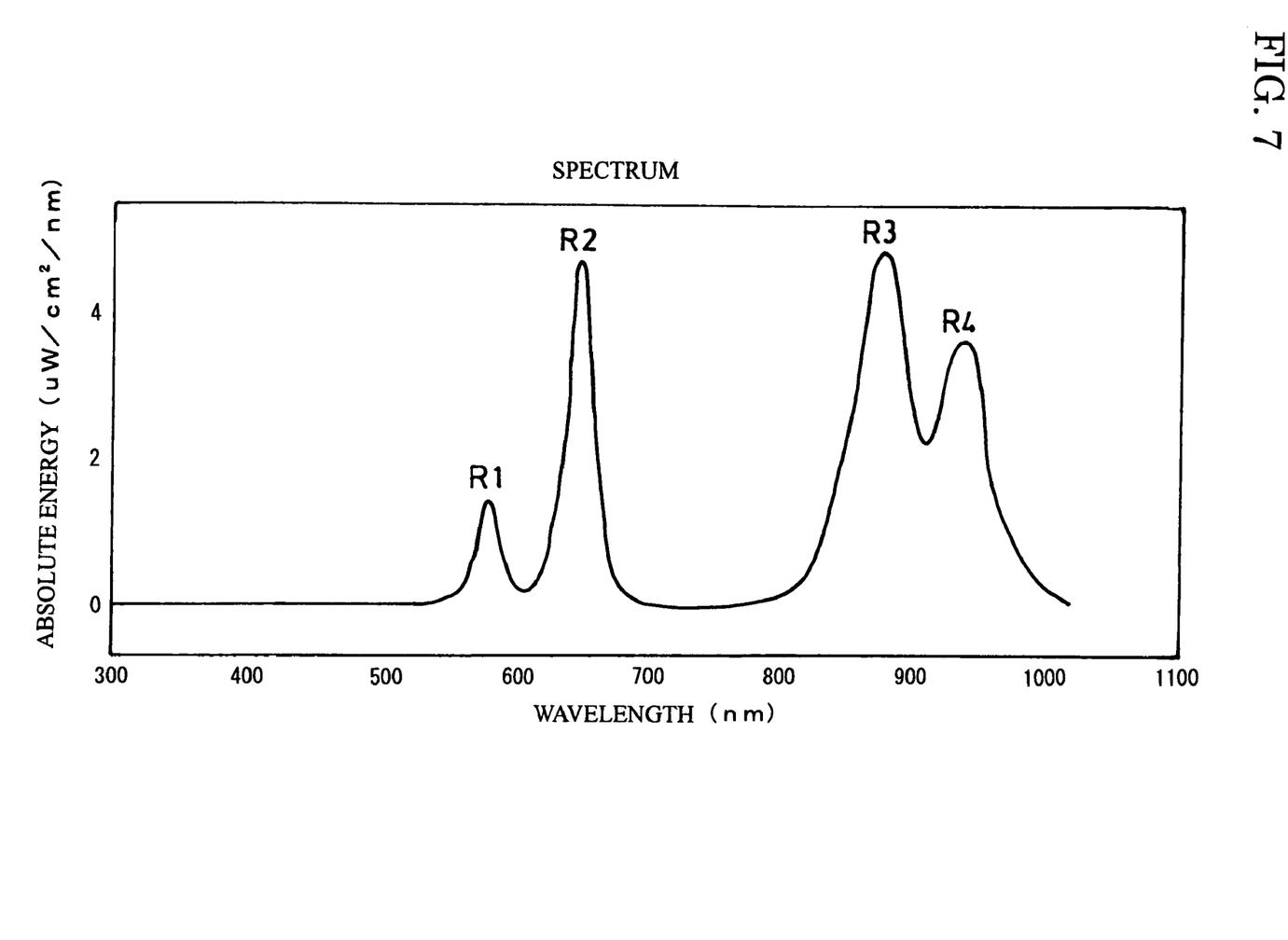
FIG. 7 is a graph illustrating a spectrum of a light source module.
Figure 8:
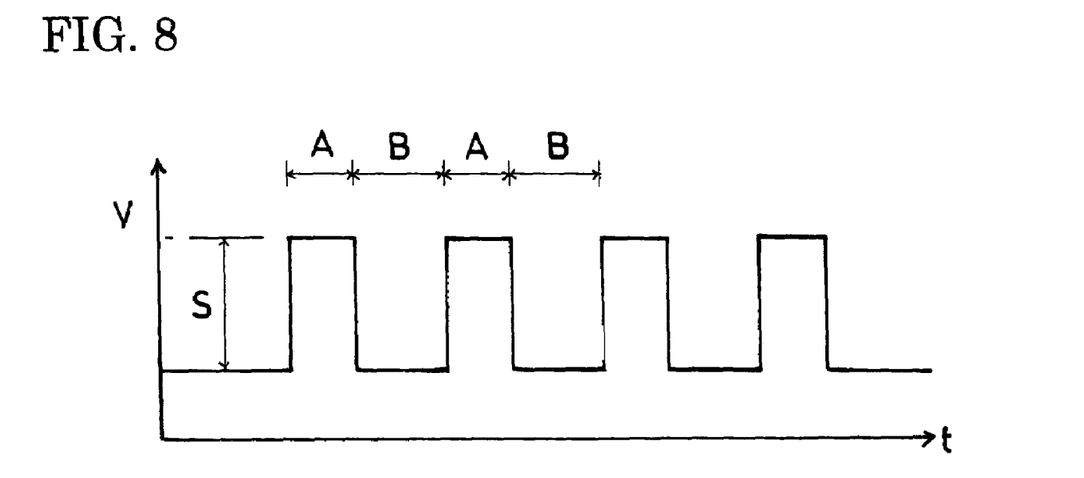
FIG. 8 is a view of a pulse signal that controls an ion generating section.

FIG. 1 is a schematic view illustrating a using state and a configuration of a beauty device according to an embodiment of the present invention; FIG. 2 is a cross-sectional view illustrating a configuration of an ion generating section; FIG. 3 is a view relating to the beauty device according to the embodiment of the present invention, where FIG. 3(a) is a side view, FIG. 3(b) is a front view, and FIG. 3(c) is a rear view; FIG. 4 is a view illustrating a light source module, where FIG. 4(a) is a plan view seen in a state that a translucent plate is detached, and FIGS. 4(b) and 4(c) are views each illustrating an array of LEDs; FIGS. 5 and 6 are views each illustrating a pulse signal that controls blinking of LEDs; FIG. 7 is a graph illustrating a spectrum of a light source module; and FIG. 8 is a view of a pulse signal that controls an ion generating section.

A beauty device 1 according to the embodiment of the present invention includes a device main body 3, a light irradiation section 5 and an ion generating section 7 that are provided at the device main body 3. The light irradiation section 5 is provided at one side surface of the device main body 3, and the ion generating section 7 is provided at the other side surface (opposite side surface) of the device main body 3, as shown in FIG. 1.

The light irradiation section 5 includes multiple LEDs (light emitting diodes), a light control section that controls emission of these LEDs, and a translucent plate 9. The translucent plate 9 is attached to the device main body 3 to be detachable therefrom.

The translucent plate 9 transmits light from the LEDs to an external section. The translucent plate 9 has complicated concave and convex portions on its surface to scatter light emitted from the LEDs. In addition, the translucent plate 9 may be a polarizing plate that transmits only light in a predetermined direction.

The device main body 3 is of a size that can be held in a user's hand, and a metal-made (metallic) battery holder 15 with conductivity is provided at one side surface, on which side the light irradiation section 5 is provided. The battery holder 15 is opened to install batteries therein. As shown in FIG. 3(c), a control panel 17 is provided at the other side surface, on which side the ion generating section 7 is provided. The control panel 17 has an ON/OFF switch and a control switch for various types of levels (L1, L2, L3).

As shown in FIG. 2, the ion generating section 7 includes a metal-made base portion 19 and a resin-made cotton holder 21 that form one electrode, and the metal-made battery holder 15 serves as the other electrode. Moreover, an ion control section 23 built in the device main body 3 controls a voltage and pulse that are applied to the base portion (one electrode) 19 and the battery holder (other electrode) 15.

The base portion 19 of the ion control section 23 is projected from the cotton holder 21. The base portion 19 is covered with a cloth 16 impregnated with a vitamin solution and held thereto by the cotton holder 21.

As illustrated in FIG. 4(a) showing a state in which the translucent plate 9 is detached, in the light irradiation section 5, four light source modules 25A and 25B (two in each) are arranged to form a diamond shape, and each light source module has multiple LEDs 20a to 20d, as shown in FIGS. 4(b) and 4(c).

Four light source modules 25A and 25B, each having a substantially circular shape, are mounted in a predetermined array on a substrate on which the respective elements of an electric circuit are contained.

As illustrated in FIGS. 4(b) and (c), each of the light source modules 25A and 25B has multiple LEDs 20a to 20d. Nine LEDs 20a to 20d in all are placed in each of the light source modules 25A and 25B, which emit light with two or more wavelengths, in a predetermined array. More specifically, the light source module 25A has three first LEDs 20a that emit red light with a wavelength of 644 nm, three second LEDs 20b that emit yellow light with a wavelength of 575 nm, and three fourth LEDs that emit near infrared light with a wavelength of 870 nm. The light source module 25B has three third LEDs 20c that emit near infrared light with a wavelength of 940 nm in place of the fourth LEDs 20d of the light source module 25A.

In the present invention, the light irradiation section 5 has multiple light source modules 25 arranged in a predetermined array, and each light source module 25 has multiple light emitting diodes (LEDs) 20a to 20d that are arranged in a predetermined array to emit light of two or more wavelengths. Accordingly, when the light irradiation selection 5 is put onto a user's skin, a fibroblast is stimulated by light of two or more wavelengths to make it possible to sufficiently reduce wrinkles and blemishes. Moreover, since no ultraviolet ray is emitted, a fixed skill (with expert knowledge) is not required at the time of using the device, making it possible to safely use the device at home.

An explanation will be next given of blinking control of the respective LEDs 20a to 20d at the light control section 13. In the present embodiment, the form of control can be switched to three levels of L1 to L3 by a selection switch, and LEDs 20a to 20d are controlled to be blinked with a cycle illustrated in FIGS. 5 and 6 and Table 1 shown below. Moreover, blinking control of each LED in E of FIG. 5 is illustrated in FIG. 6. Additionally, in FIG. 6, a frequency is 5 KHz, a pulse width n and a pulse distance m are 100 μs, respectively, As explained in the present embodiment, LEDs 20a to 20d each having a different frequency are controlled to be blinked with a time difference to irradiate light of each wavelength efficiently and provide an effective stimulus to a user's skin.

TABLE 1

|  | E | F | Frequency |
|---|---|---|---|
| L1 | 10 ms (mili-second) | 100 ms | 9.09 Hz |
| L2 | 20 ms | 140 ms | 6.25 Hz |
| L3 | 30 ms | 150 ms | 5.55 Hz |

In the present embodiment, the light pulse control width and distance are thus set to values in a small range of micro second order, thereby making it to possible to promote absorption of light and stimulus onto the user'skin. Also, the skin is efficiently stimulated and light is penetrated to make it possible to improve the user's skin. Moreover, the user's skin is irradiated with light of each wavelength, thereby bringing about an effect that reduces blemishes of the respective colors on the skin.

An explanation will be next given of the ion generating section 7. In the ion generating section 7, the annular cotton holder 21 is jointed to the base portion 19 that forms one electrode, and the base portion 19 is covered with the cloth 16 impregnated with the vitamin solution so that the cloth 16 is held to the base portion 19 by the cotton holder 21.

A predetermined pulse voltage is supplied to the base portion 19 as one electrode and the battery holder 15 as the other electrode by the ion control section 23. As illustrated in FIG. 8, the pulse voltage to be supplied is voltage S and pulse width A μs (micro second) and pulse distance B μs are used.

In addition, a plus and minus of the voltages to be supplied to the electrodes 19 and 15 can be switched. Moreover, plus and minus voltages are made to flow alternately, so that stimulation to the skin may be reduced.

In the present embodiment, three levels of L1 to L3 can be switched by the selection switches, and values at the respective levels L1 to L3 are shown by Table 2 described below. In addition, the voltage S is 5 V and the frequency is 1 KHz.

TABLE 2

|    | A      | B      |
|----|--------|--------|
| L1 | 300 μs | 700 μs |
| L2 | 400 μs | 600 μs |
| L3 | 500 μs | 500 μs |

An explanation will be next given of the method of using the and function of the beauty device 1 according to the present embodiment.

In the present beauty device 1, it is desirable that the light irradiation section 5 and the ion generating section 7 be used alternately. For example, the light irradiation section 5 is put onto the skin such as a face, particularly, locations on the skin where annoying blemishes and wrinkles are present, for several minutes, the cloth that is impregnated with the vitamin solution is thereafter attached to the ion generating section 7, and the ion generating section 7 is next put onto the skin.

In the ion generating section 7, electrical conduction occurs on the skin surface from the hand that holds the base portion 19 as one electrode and the battery holder 15 as the other electrode, and a potential difference occurs between the skin and the base portion 19 to generate an ion between the skin and the base portion 19. Particularly, in the present embodiment, since the cloth that is impregnated with the vitamin solution is attached to the ion generating section 7, the solution is also ionized to promote absorption onto the skin. Moreover, this makes it easy to reveal fine dirt and dust adhered on the skin, so that a facial cleansing effect is also promoted.

Although, in the light irradiation section 5, stimulus is given to the skin by light of each wavelength on the other hand, the effect and function of each wavelength will be explained with reference to FIG. 7.

A wavelength R1 of 575 nm stimulates a tranquilizing nerve block in the skin and also stimulates a fibroblast to cause a collagen proliferation function. Moreover, this is excellent in improving the skin.

A wavelength R2 of 644 nm stimulates the tranquilizing nerve block in the skin and also stimulates the fibroblast to cause the collagen proliferation function, similar to the wavelength R1 of 575 nm. Moreover, this is excellent in improving a reddish skin portion or blue skin portion.

A wavelength R3 of 870 nm stimulates the tranquilizing nerve block in the skin and also stimulates the fibroblast to cause the collagen proliferation function, similar to the wavelength R1 of 575 nm. Moreover, this is excellent in improving a reddish skin portion.

A wavelength R4 of 940 nm stimulates the tranquilizing nerve block in the skin and also stimulates the fibroblast to cause the collagen proliferation function, similar to the wavelength R1 of 575 nm. Moreover, this is excellent in improving shallow wrinkles on the skin.

As mentioned above, according to the present embodiment, the ion generating section 7 and the light irradiation section 5 each having an independent effect to the skin are put onto the skin alternately, thereby producing an excellent and beautiful skin effect. Either one of the ion generating section 7 and the light irradiation section 5 may be, of course, used.

An experiment in which the beauty device 1 according to the present embodiment was put onto the skin for five minutes per day for one week was given to 10 subjects. According to the questionnaires to the subjects, a result in which blemishes on the skin disappeared or blemishes and wrinkles were reduced from seven subjects was obtained. Moreover, a result in which nine subjects felt that the skin became firm and lustrous after using the beauty device according to the present embodiment was obtained.

Furthermore, in the light irradiation section 5 of the beauty device 1, since light from each light source module 25 is scattered to apply irradiation, light can be diffused, so that blemishes and wrinkles can be reduced in a wide range by one irradiation.

In the light irradiation section 5, the light wavelengths of the adjacent light emitting diodes are different from each other. Multiple lights can be sufficiently made to interfere with one another to be irradiated, so that an excellent beauty effect can be obtained.

Furthermore, in the beauty device 1 of the present embodiment, the light emitting device 20a to 20d emit yellow light, red light and near infrared light. Yellow, red and infrared light has a good light permeability and stimulate the nerve block, so that blemishes and wrinkles can be reduced effectively.

It is needless say that the present invention is not limited to the aforementioned embodiment and various modifications may be possible without departing from the broad spirit and scope of the invention. For example, in the ion generating section 7, a cloth, which is impregnated with a cosmetic lotion without vitamins on the market, or only water may be used.

Various embodiments and changes may be made thereunto without departing from the broad spirit and scope of the invention. The above-described embodiment is intended to illustrate the present invention, not to limit the scope of the present invention. The scope of the present invention is shown by the attached claims rather than the embodiment described above. Various modifications made within the meaning of an equivalent of the claims of the invention and within the claims are to be regarded to be within the scope of the present invention.

This application is based on Japanese Patent Application 2003-414886 filed on Dec. 12, 2003 and including a specification, claims, drawings and summary. The disclosure of the above Japanese Patent Application is incorporated herein by reference in its entirety.

What is claimed is:

1. A beauty device comprising:
   a light irradiation section for irradiating light of a predetermined wavelength; and
   an ion generating section for generating an ion,
   wherein said light irradiation section is placed at one side surface of a main body of said beauty device and said ion generating section is placed at the other side surface of the main body of said beauty device;
   wherein said light irradiation section includes a plurality of light source modules arranged in a predetermined array; and
   wherein each light source module includes a plurality of light emitting diodes that are arranged in a predetermined array to emit light of two or more wavelengths.

2. The beauty device according to claim 1, wherein said ion generating section includes one electrode to which a cloth impregnated with a vitamin solution is attached, another other electrode provided at a holding section of the main body, a power source, and an ion control section; and
   wherein said ion control section is operable to apply a pulse wave of a predetermined voltage between the one electrode and the other electrode.

3. The beauty device according to claim 2, wherein said ion control section is operable to apply the pulse wave of voltage of 3 to 10 V with a frequency of 0.5 to 2 KHz, a distance of 500 to 700 μs and a width of 300 to 500 μs per pulse.

4. The beauty device according to claim 3, wherein said ion control section is operable to provide a plurality of pulse widths and pulse distances.

5. The beauty device according to claim 1, wherein said light emitting diodes are operable to emit yellow light, red light and infrared light at a predetermined pulse.

6. The beauty device according to claim 5, wherein said light emitting diodes are operable to emit light of the respective colors with a time difference for each color.

* * * * *